US007129328B2

United States Patent
Farnham et al.

(10) Patent No.: US 7,129,328 B2
(45) Date of Patent: Oct. 31, 2006

(54) LIVER TUMOR MARKER SEQUENCES

(75) Inventors: Peggy J. Farnham, Madison, WI (US); Carrie R. Graveel, Grand Rapids, MI (US); Sarah R. Harkins-Perry, Monona, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 367 days.

(21) Appl. No.: 10/620,532

(22) Filed: Jul. 16, 2003

(65) Prior Publication Data

US 2004/0086916 A1    May 6, 2004

Related U.S. Application Data

(60) Provisional application No. 60/396,626, filed on Jul. 17, 2002.

(51) Int. Cl.
*C07K 1/00*    (2006.01)
*A61K 39/00*    (2006.01)

(52) U.S. Cl. .................................. 530/350; 424/185.1
(58) Field of Classification Search ................ 530/350; 424/185.1
See application file for complete search history.

(56) References Cited

U.S. PATENT DOCUMENTS

2002/0115094 A1    8/2002    Farnham et al.

2004/0029790 A1 *    2/2004    Patturajan et al. ............ 514/12

OTHER PUBLICATIONS

Alberts et al. (Molecular Biology of the Cell, 3rd edition, 1994, p. 465).*
Lewin, B. (Genes VI, Oxford University Press, Inc., NY, Chapter 29, 1997).*
Fu et al (EMBO Journal, 1996, vol. 15, pp. 4392-4401).*
Mallampalli et al. (Biochem. J. vol. 318, 1996, pp. 333-341).*
Greenbaum et al. (Genome Biology, 2003, vol. 4, Issue 9, pp. 117.1-117.8).*
Graveel CR, Jatkoe T, Madore SJ, Holt AL, Farnham PJ. Expression profiling and identification of novel genes in hepatocellular carcinomas. Oncogene. May 10, 2001;20(21):2704-12.

* cited by examiner

*Primary Examiner*—Jeffrey Siew
*Assistant Examiner*—Sean E Aeder
(74) *Attorney, Agent, or Firm*—Quarles & Brady, LLP

(57) ABSTRACT

Polypeptides whose expression is upregulated in liver tumor cells and cells from liver preneoplastic foci relative to expression in normal liver cells are disclosed as are polynucleotides that encode the polypeptides. In humans, the polynucleotide maps to a region of chromosome 15. The overexpression has also been confirmed in human liver, breast, colon and kidney cancer cell lines. It is believed that the polypeptides are overexpressed in tumor and preneoplastic cells in general.

4 Claims, 4 Drawing Sheets

LIVER TUMOR MARKER SEQUENCES

CROSS-REFERENCE TO RELATED APPLICATIONS

This application claims priority to U.S. provisional application Ser. No. 60/396,626, filed on Jul. 17, 2002, which is herein incorporated by reference in its entirety.

STATEMENT REGARDING FEDERALLY SPONSORED RESEARCH OR DEVELOPMENT

This invention was made with U.S. Government Support from the following agency: NIH, Grant No. CA22484. The U.S. Government has certain rights in the invention.

BACKGROUND OF THE INVENTION

Primary liver cancer is the fifth most common cancer worldwide with approximately half a million cases reported in 1990. Hepatocellular carcinoma (HCC) accounts for 80% of all liver cancer and the rates of HCC have increased by over 70% in the last two decades in the U.S. The fatality ratio (mortality/incidence) of liver cancer is approximately 1, indicating that the majority of patients live less than a year. Late diagnosis due to lack of clinical symptoms is one of the main reasons for the high fatality ratio.

Liver cancer can result from both viral infection and chemical exposure. Known risk factors include hepatitis B and C virus infection and exposure to aflatoxin β1. It is not known whether distinct routes to liver cancer affect the same or different cellular pathways. No mutational model has yet been developed for liver cancer as it has been for other cancers such as colon cancer. The molecular events that precede neoplastic transformation of the liver are not well understood. With no clearly identified cause, successful treatment options are lacking. In fact, the specific genes that are deregulated in liver cancer have not yet been enumerated. This is a critical first step in developing a successful strategy for treating liver cancer.

There is a pressing need to understand the molecular events associated with the development of liver cancer, both in humans and in animal model systems where liver cancer is extensively studied, and to provide diagnostic and therapeutic reagents for treating same.

BRIEF SUMMARY OF THE INVENTION

The invention is summarized in that polypeptides of the invention are found in liver tumor cells and in cells from preneoplastic liver foci in human and non-human animals at levels higher than are found in regenerating or quiescent normal liver tissue. This finding has been confirmed in human breast, colon and kidney cancer cell lines. As a result of this differential overexpression, the polypeptides, as wells as polynucleotides that encode the polypeptides, are diagnostic markers for cancer in general, especially liver, breast, colon and kidney cancer, in a human or non-human animal.

In one aspect, the present invention relates to an isolated polypeptide containing an amino acid sequence of SEQ ID NO:2, an amino acid sequence that is at least 70% identical to SEQ ID NO:2 over the length of SEQ ID NO:2, an amino acid sequence of amino acid 22 to amino acid 439 of SEQ ID NO:2 (secreted portion of SEQ ID NO:2), an amino acid sequence that is at least about 68% identical to amino acid 22 to amino acid 439 of SEQ ID NO:2 over the length of amino acid 22 to amino acid 439 of SEQ ID NO:2, an amino acid sequence of SEQ ID NO:4, an amino acid sequence that is at least 70% identical to SEQ ID NO:4 over the length of SEQ ID NO:4, an amino acid sequence of amino acid 22 to amino acid 400 of SEQ ID NO:4 (secreted portion of SEQ ID NO:4), an amino acid sequence that is at least about 68% identical to amino acid 22 to amino acid 400 of SEQ ID NO:4 over the length of amino acid 22 to amino acid 400 of SEQ ID NO:4. The percentage identity of sequences is determined using the Blosum62 alignment method.

In another aspect, the invention also relates to an isolated nucleic acid containing a polynucleotide that encodes a polypeptide of the invention, to a complement of the polynucleotide, or to a polynucleotide that is at least about 80% identical, more preferably 90% identical, and still more preferably 95% identical to an aforementioned polynucleotide of the invention, using the Wilbur-Lipman DNA Alignment method. A polynucleotide that encodes a polypeptide of the invention can include but is not limited to SEQ ID NO:1 from nucleotide 25 to nucleotide 1341, which encodes SEQ ID NO:2, as well as SEQ ID NO:3 from nucleotide 1 to nucleotide 1200, which encodes SEQ ID NO:4. SEQ ID NO:3, predicted by the inventors to represent a coding region on human chromosome 15 (contig Hs15_10351), is 82.4% identical to the polypeptide-encoding portion of SEQ ID NO:1 using the Wilbur-Lipman DNA Alignment method.

In another aspect, a polynucleotide of the invention is engineered into a genetic construct downstream from a heterologous promoter not natively upstream of the polynucleotide that directs transcription of the polynucleotide. The genetic construct is introduced into a host cell that supports transcription of the polynucleotide and translation of the encoded polypeptide which can then be purified using methods known to those skilled in the art. Alternatively, the construct comprising a polynucleotide of the invention is provided in an in vitro transcription/translation system for producing the encoded polypeptide.

In yet another aspect, the present invention provides a host cell transfected with a genetic construct of the invention.

In still another aspect, the invention is an antibody that specifically binds to a polypeptide of the invention.

In yet another aspect, the invention is a method for identifying an agent that modulates the expression of a polypeptide of the invention (e.g., an inducer or suppressor). The method includes the steps of exposing a cell that contains a polynucleotide of the invention under the control of its native promoter, measuring the expression of the polynucleotide in the cell, and comparing the expression to that in a control cell that is not exposed to the test agent. A higher or lower than the expression in the control cell indicates that the agent can modulate the expression of the polynucleotide. The expression can be measured and compared at either the mRNA level or the protein level. Preferably, a liver, breast, colon or kidney cell (cancerous or normal) is used in the method. More preferably, a human or murine liver, breast, colon or kidney cell is used.

In still another aspect, the present invention is a method of diagnosing cancer or preneoplastic development in a tissue or organ of a human or non-human animal by measuring the expression of a polypeptide of the invention in cells of the tissue or organ obtained from a region suspected of cancer or preneoplastic development, and comparing the expression to a normal standard, wherein a higher than normal expression indicates cancer or preneoplastic development in the suspected region. A skilled artisan can readily establish a normal standard. For example, it can be the expression level in normal cells of the same tissue or organ in the same animal, or it can be an expression level range established by testing normal cells of the same tissue or organ of other animals of the same species. The expression can be measured and compared at either the mRNA level or protein level.

In a related aspect, the present invention is a method for identifying a candidate human or non-human animal for further cancer screening, where the method includes, in one embodiment, the step of determining the level of a polypeptide of the invention in a blood or blood-derived sample from the animal, whereby the animal is identified as a candidate for further cancer screening when the level exceeds either a normal range established by the same animal during a period that is tumor-free in the tissue or organ, or a normal range established by other animals of the same species that are tumor-free in the tissue or organ. In another embodiment, the method takes advantage of the expected secretion of the polypeptide and the development of antibodies to the polypeptide in a human or non-human animal that overexpresses the polypeptide in the cancerous or preneoplastic tissue or organ. The method includes the step of determining the level of an antibody to the polypeptide in a blood or blood-derived sample from the animal, whereby the animal is identified as a candidate for further cancer screening when the antibody level exceeds either a normal range established by the same animal during a period that is tumor-free in the tissue or organ, or a normal range established by other animals of the same species that are tumor-free in the tissue or organ. It is understood that individuals free of cancer or preneoplastic development in the tissue or organ may not develop an antibody to the polypeptide. Thus, the normal range for the level of the antibody can be zero.

In still another aspect, the invention relates to a kit suitable for use in a method for determining the level of a polypeptide or polynucleotide of the invention, where the kit contains at least one of an antibody specifically directed to an epitope on a polypeptide of the invention and a polynucleotide that hybridizes to a polynucleotide of the invention, as well as at least one control sample component for which the relative or absolute amount of the polynucleotide or polypeptide of the present invention is known, the control sample component being selected from liver cancer cells, preneoplastic liver cells, normal liver cells, breast cancer cells, normal breast cells, colon cancer cells, normal colon cells, kidney cancer cells, normal kidney cells, an extract of any of the foregoing cells, a blood sample from a human or non-human animal, and a blood-derived sample from a human or non-human animal.

It is an object of the present invention to provide a polynucleotide and a polypeptide that are differentially expressed in preneoplastic or cancer cells and normal regenerating or quiescent cells in a tissue or organ of a human and non-human animal.

Other objects, features and advantages of the present invention will become apparent upon consideration of the following detailed description of the invention.

DETAILED DESCRIPTION OF THE INVENTION

Figure 1:
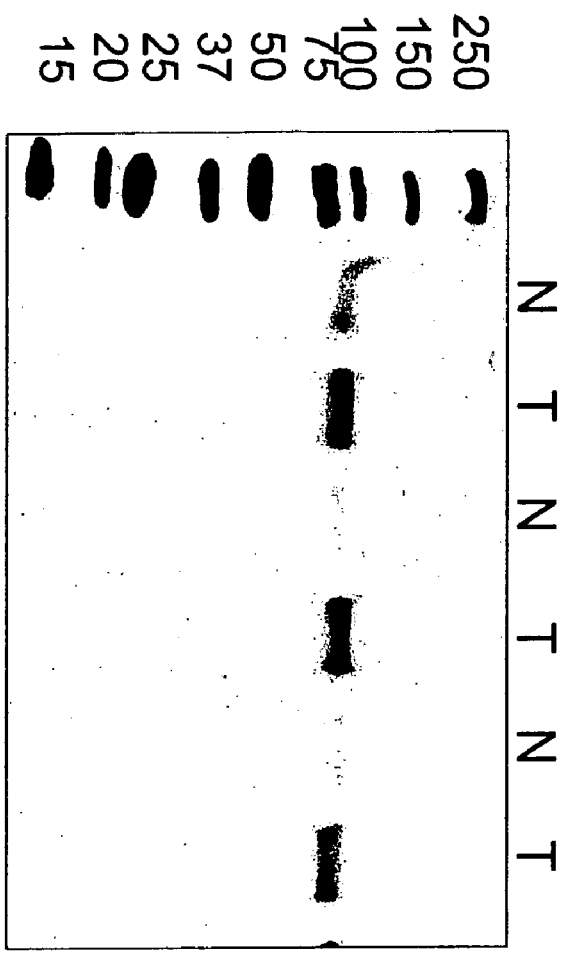
FIG. 1 shows the cloning of CRG-L2. a) RT-PCR analysis of CRG-L2 in mouse liver tissues. Because the C3H/HeJ mice used in these studies are inbred, all untreated mice are genetically identical. Accordingly, we have never observed any differences in CRG-L2 expression in comparison of individual normal mice. Therefore, quiescent, regenerating, and newborn RNA samples were prepared from several mice and then pooled so that the same pooled RNA samples could be used in multiple experiments. Quiescent and regenerating samples are a combination of four livers and newborn samples are a combination of eight livers. However, it is known that tumors display heterogeneous genetic and molecular profiles. Therefore, to take into consideration these possible differences, the tumor samples used in our experiments are from individual mice. b) mRNA structure of CRG-L2. Alignment of the 5' and 3' RACE products suggest that CRG-L2 mRNA can contain one of three alternative 3'UTRs. c) Northern blot hybridization of CRG-L2 in quiescent liver and four individual liver tumors. Four bands were detected at 2.4, 3.0, 5.5, and 10 kb mRNAs. The three smaller mRNAs correspond to clones A, B, and C. A fourth band, D, was not cloned probably due to inefficient PCR through a long 3' UTR. d) The CRG-L2 open reading frame was aligned to mouse chromosome 9 (31 cM). Exons are represented by black boxes. The distance between some of the exons is estimated since there are gaps between the contigs in the genome and these gaps are represented by a >sign. CRG-L2 is localized within chromosome 15q21.2 of the human genome and a similar intron/exon structure is suggested by comparing the mouse cDNA to the human genome.

Liver cancer is generally studied in animal model systems, preferably in rodent systems, where certain strains are bred for high susceptibility to liver tumors. C3H/HeJ mice are highly susceptible to liver tumors after induction with diethylnitrosamine (DEN). To identify polynucleotide sequences or genes that show differential expression in liver tumor cells as compared to normal liver cells, gene expression differences between liver tumors and a regenerating liver were determined using representational difference analysis (RDA: Lisitsyn, et al., *Science* 259:946 (1993), incorporated by reference as if set forth herein in its entirety).

In this application, the applicants disclose polypeptides from murine animals (SEQ ID NO:2) and humans (SEQ ID NO:4) that are upregulated in cells and cell extracts from human and murine liver tumors and liver preneoplastic tissues, relative to quiescent and regenerating normal liver cells. The polypeptide is therefore given the name human or murine Cancer Related Gene-Liver 2 (CRG-L2). CRG-L2 overexpression was also found in human liver, breast, colon and kidney cancer cell lines. Thus, despite of its name indicative of liver origin, it is believed to be overexpressed in other types of cancer and preneoplastic cells in general, especially breast, colon and kidney cancer and preneoplastic cells.

Using the Blosum62 alignment method, the human and murine CRG-L2s are found to be 76% identical. It is expected that CRG-L2s from other animals, e.g., other mammals, are at least 70% identical to either the human or murine CRG-L2 if compared using the same alignment method. Hydrophobic sequences are present within the first 30 amino acids of SEQ ID NO:2 and SEQ ID NO:4. Based on information obtained from other proteins with leader sequences, the serine at amino acid position 21 of both SEQ ID NO:2 and SEQ ID NO:4 is believed to be the cleavage site of a leader sequence for the secretion of both of the CRG-L2s. Accordingly, it is believed that when amino acids 1–21 are cleaved, the remaining amino acid sequences of SEQ ID NO:2 and SEQ ID NO:4 can be secreted from cells. Corresponding leader sequences on other CRG-L2s can be readily identified by a skilled artisan. Depending on the variability of the leader sequences among CRG-L2s, the percentage of identity among the secreted sequences may be about 3% higher or lower than the overall 70% identity. Generally speaking, it is expected that the secreted portion of CRG-L2s in other animals, e.g., other mammalians, are at least about 68% identical to either the secreted portion of the human or that of the murine CRG-L2.

Also disclosed are polynucleotides that encode the polypeptides of the invention (e.g., the full length and the secreted CRG-L2s), which can include, without limitation, mRNA, single or double stranded DNA, cDNA and the like. In addition to the primary murine cDNA product disclosed as SEQ ID NO:1, two additional variant murine cDNAs that are believed to derive from alternative 3' untranslated regions were also obtained. The variant murine cDNA molecules differ from SEQ ID NO:1 in the 3' untranslated portion of the molecules, commencing respectively at nucleotide 1937 and at nucleotide 2342, as shown in the Sequence Listing. SEQ ID NO:3 discloses a sequence from human Chromosome 15 that encodes the human CRG-L2 of SEQ ID NO:4.

Further, the invention provides materials and methods for detecting expression (and changes in expression) of the polypeptides and of the polynucleotides that encode the polypeptides, thereby facilitating use as a diagnostic marker for cancer and preneoplastic development and as a system for assessing putative therapeutic agents. As described in detail in the example below, since the CRG-L2 either belongs or is similar to the family of cancer-testis antigens, it is expected that a patient will display an immune response to CRG-L2 when it is overexpressed in preneoplastic and cancerous tissues. Therefore, detecting or measuring the level of an antibody to CRG-L2 in a blood or blood-derived sample from a patient provides another diagnostic tool.

Structurally, the murine CRG-L2 protein (SEQ ID NO:2) contains 439 amino acids and has a predicted molecular weight of about 47.5 kDA. Using the Simple Modular Architecture Research Tool (available on the world wide web courtesy of the European Molecular Biology Laboratory—Heidelberg), it was determined that the murine CRG-L2 includes two collagen domains in the 5' region (corresponding to amino acids 29–88 and 89–149 of SEQ ID NO:2, respectively) and a large olfactomedin domain near the C-terminus (corresponding to amino acids 189–433 of SEQ ID NO:2). The human protein also contains two putative collagen domains and one olfactomedin domain at amino acids 27–85, 86–145, and 177–395 of SEQ ID NO:4, respectively. Olfactomedin-related proteins are secreted glycoproteins having conserved C terminal motifs. It is anticipated that CRG-L2 can be secreted into the blood and an increase in blood CRG-L2 level over normal levels is diagnostic of cancer and preneoplastic development. Preferably, the diagnostic blood CRG-L2 level is set to be at least about 5%, more preferably at least about 10%, and most preferably at least about 25% over a normal level.

The term "isolated nucleic acid" or "isolated polypeptide" used in the specification and claims of the present invention means a nucleic acid or polypeptide isolated from its natural environment or prepared using synthetic methods such as those known to one of ordinary skill in the art. Complete purification is not required in either case. Amino acid and nucleotide sequences that flank a polypeptide or polynucleotide that occurs in nature, respectively, can but need not be absent from the isolated form. The polypeptides and nucleic acids of the invention can be isolated and purified from normally associated material in conventional ways such that in the purified preparation the polypeptide or nucleic acid is the predominant species in the preparation. At the very least, the degree of purification is such that the extraneous material in the preparation does not interfere with use of the polypeptide or nucleic acid of the invention in the manner disclosed herein. The polypeptide or nucleic acid is preferably at least about 85% pure, more preferably at least about 95% pure and most preferably at least about 99% pure.

Further, an isolated nucleic acid has a structure that is not identical to that of any naturally occurring polynucleotide or to that of any fragment of a naturally occurring genomic polynucleotide spanning more than three separate genes. An isolated nucleic acid also includes, without limitation, (a) a polynucleotide having a sequence of a naturally occurring genomic or extrachromosomal nucleic acid molecule but which is not flanked by the coding sequences that flank the sequence in its natural position; (b) a polynucleotide incorporated into a vector or into a prokaryote or eukaryote genome such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are polynucleotides present in mixtures of clones, e.g., as these occur in a DNA library such as a cDNA or genomic DNA library. An isolated nucleic acid can be modified or unmodified DNA or RNA, whether fully or partially single-stranded or double-stranded or even triple-stranded. A nucleic acid can be chemically or enzymatically modified and can include so-called non-standard bases such as inosine.

The nucleotide sequences of the invention can be introduced into, and expressed in, host cells which can be prokaryotic (such as bacterial) cells or eukaryotic (such as yeast, insect, amphibian or mammalian) cells whereupon the transcription of polynucleotide and the properties of the encoded polypeptides can be assessed.

The disclosure of the CRG-L2 sequences that are upregulated in liver tumor and preneoplastic cells, and in human breast, colon and kidney cancer cell lines provides a means for identifying (in vivo or in vitro) candidates for further testing as preventive and therapeutic agents. For example, animal cells that contain a CRG-L2 sequence under the control of its native promoter can be exposed to a test agent and the effect of the test agent on the CRG-L2's expression at the mRNA or protein level relative to that of untreated controls can be measured. Alternatively, the level of expression can be assessed in biological samples taken directly from a human or non-human tissue. Presumably, an anti-tumor agent can bring down the mRNA and protein level in tumor cells. Accordingly, an agent that demonstrates such an activity is a good candidate for further testing for anti-tumor efficacy.

The presence and level of such a differentially expressed protein can be readily discerned using antibodies directed to an epitope on the protein using well known methods, such as an ELISA method. It is well within the skill of one of ordinary skill in the art to generate such antibodies. The presence and level of mRNA for the protein can be measured using methods for hybridizing nucleic acids (including, without limitation, RNA, DNA, and cDNA). Such methods are generally known to those skilled in the art, but are enabled by the disclosure herein of a tumor-specific sequence. Examples of such methods include but are not limited to RT-PCR amplification, Northern blot and Southern blot.

Given the disclosure herein of polynucleotides that encode CRG-L2 of human, murine and other animal species, one of ordinary skill in the art knows how to design primers for use in RT-PCR analysis and probes for Northern and Southern blot. The Example below describes a method of using RT-PCR to measure CRG-L2 mRNA level in liver tumor cells, liver preneoplastic cells and normal liver cells. The RT-PCR amplified a fragment of CRG-L2 cDNA (SEQ ID NO: 1) and its noted 3' end variants, and the mRNA level in liver tumor and preneoplastic cells was observed to be higher than that in normal liver cells. Accordingly, a suitable CRG-L2 sequence for amplifying or probing in analyzing differential CRG-L2 mRNA levels is one that corresponds to a fragment shared by all three CRG-L2 cDNA sequences. A CRG-L2 mRNA sequence that corresponds to a fragment unique to the longer 3' untranslated sequence variants could also be used to analyze differential CRG-L2 mRNA expression since Northern analysis has shown that all three mRNAs are differentially expressed in liver tumor and preneoplastic cells relative to normal liver cells.

A skilled artisan understands that the polynucleotides disclosed herein can contain additional nucleotides at the 5'-end, 3'-end or both that do not affect the function of the polynucleotides in terms of their uses contemplated herein. The additional nucleotides can but do not have to assist in the cloning, detection and purification procedures associated with the use of the polynucleotides. Similarly, a skilled artisan understands that the polypeptides disclosed herein can contain additional amino acid sequences at the N- or C-terminus or both that do not affect the function of the polypeptides. The additional amino acid sequences can but do not have to assist in purification, detection, or stabilization of the polypeptides.

Further, a skilled artisan understands that polynucleotide and polypeptide sequences presented herein can vary somewhat, whether as a result, e.g., of sequencing error or allelic variation or duplication, from the sequence presented while still retaining their essential nature, that is, higher expression level in tumor and preneoplastic cells relative to normal cells. Further, the polynucleotides of the invention include conservatively modified variants of the sequences presented herein, complementary sequences, and splice variants. In view of the known degeneracy in the genetic code, the proteins or polypeptides disclosed can also be encoded by a large number of other polynucleotide sequences, all of which are within the scope of the invention. Polynucleotide sequences that are at least 80% identical to the polynucleotide sequences that encode the polypeptide sequences disclosed herein can be used as hybridization probes for coding sequences and are thus within the scope of the present invention. The polynucleotides and polypeptides of the invention include, without limitation, polymorphic variants, alleles, mutants, and interspecies homologs that (1) are expressed at higher level in tumor and preneoplastic cells, especially in liver, breast, colon and kidney tumor and preneoplastic cells, (2) bind to antibodies raised against the coding region of the disclosed polypeptides, (3) specifically hybridize under stringent or moderately stringent hybridization conditions to a polynucleotide that encodes a polypeptide of the present invention, or (4) are amplified by primers that amplify a polynucleotide that encodes a polypeptide of the present invention.

Exemplary stringent hybridization conditions include 50% formamide, 5×SSC and 1% SDS incubated at 42° C., or 5×SSC and 1% SDS incubated at 65° C., followed by washing in 0.2×SSC and 0.1% SDS at 65° C. Exemplary moderately stringent hybridization conditions include 40% formamide, 1M NaCl and 1% SDS incubated at 37° C. followed by washing in 1×SSC at 45° C. These conditions are merely exemplary as one skilled in the art is readily able to discern stringent from moderately stringent hybridization conditions.

Moreover, the sequences of the invention also encompass substitutions, additions and deletions of the sequences presented where the change affects one or a few amino acids in the presented polypeptide sequences, without substantial effect upon the activity of the polypeptide, i.e., differential expression in cancer cells and preneoplastic cells relative to normal cells.

The present invention will be better understood upon consideration of the following non-limiting example.

EXAMPLE

Materials and Methods

Rapid Amplification of cDNA Ends (RACE). Rapid amplification of cDNA ends (RACE) was performed in both directions using the SMART cDNA amplification kit (Clontech) from mouse liver tumor polyA RNA. 5' and 3' RACE were performed using the gene-specific primers, GSP-A [5'-GCATGGCAAGAACAGACTGG-3'] (SEQ ID NO:5) and GSP-B [5'-GGATGAGAAGGGCATCTGGA-3'] (SEQ ID NO:6). 5' and 3' RACE products that were identified with the corresponding GSP primer were gel extracted and cloned into TOPO-TA vector (Invitrogen). Cloned products were sequenced by Big Dye (ABI) in the McArdle Laboratory Sequencing Facility (University of Wisconsin-Madison).

RNA Analysis. For analysis of murine CRG-L2 mRNA, total RNA was extracted from liver using guanidine thiocyanate/CsCl as described previously in (Lukas et al., 1999, incorporated by reference in its entirety). PolyA mRNA was isolated from 250 µg of total RNA using Oligotex mRNA Kit (Qiagen). RT-PCR was performed as described previously (Graveel et al., 2001, incorporated by reference in its entirety) with primers, RDA-3a [5'-CAACAACCTGGCTAGAGC-3'] (SEQ ID NO:7) and RDA-3b [5'-GCCATCTGATGCTCTATCC-3'] (SEQ ID NO:8).

For Northern blot hybridization, polyA RNA samples (2 µg) were prepared and electrophoresed as described previously (Lukas et al., 1999). Gel was soaked in 5 volumes of water for 5 min and then transferred overnight to a Gene-Screen (NEN Life Science Products) membrane in 10×SSC.

Membrane was UV crosslinked twice (120 mJ) and baked in a vacuum for 2 h at 80° C. Membrane was prehybridized at 42° C. overnight in hybridization solution [50% formamide, 5× Denhardt's solution, 1% SDS, 10% dextran sulfate, 1 mg sonicated salmon sperm DNA (boiled), 5× standard saline phosphate with EDTA (SSPE)]. Probes were labeled by nick translation (Rigby et al., 1977). A fragment of CRG-L2 (nucleotides 188–1243 of SEQ ID NO:1) was released with EcoRI from the pCR-TOPO4 vector. $^{32}$P-labeled probe was added to the hybridization buffer and hybridized overnight at 42° C. Blots were washed-at RT in 2×SSPE for 30 min and at 65° C. for 45 min in 2×SSPE, 2% SDS. Signals were visualized by autoradiography or phosphoimagery.

For analysis of CRG-L2 in human tissue, RT-PCR was performed for 25 cycles with primers hCRGL2a [5'-CATGGCAAGAACAGACTGGG-3'] (SEQ ID NO:9) and hCRGL2b [5'-GCCAGGAAACATCCCAAACTC-3'] (SEQ ID NO:10) and 10 µL of the reaction was electrophoresed on a 1% agarose/EtBr gel. The gels were soaked in 1×TAE for 5 min, denatured for 30 min [1.5M NaCl, 0.5M NaOH], and neutralized for 30 min [1.5M NaCl, 0.5M Tris (pH 7.2), 1 mM EDTA (pH 8.0)]. DNA was transferred to a Hybond N membrane (Amersham) with 20×SSPE overnight. The membrane was baked for 30 min at 80° C. in a vacuum oven and UV crosslinked twice (120 mJ). The membrane was prehybridized at 42° C. for 3 h in hybridization solution [50% formamide, 5% Denhardt's, 3.4×SSPE, 10% dextran sulfate, 5% SDS, 1% sarkosyl, 100 mg sonicated salmon sperm DNA (SSS), 100 mg boiled SSS]. Probes were labeled by nick translation (CRG-L2 fragment, nucleotides 188–1243 of SEQ ID NO:1) and added to the hybridization solution. Membranes were hybridized overnight at 42° C. and were washed for 20 min at RT in 2×SSPE, 01% SDS and for 2 h at 65° C. in 0.5×SSPE, 0.2% SDS. Signals were visualized by autoradiography and phosphoimagery. All primers used in this study were synthesized at the University of Wisconsin-Madison Biotechnology Center.

In Situ Hybridization. In situ hybridization was performed as described previously (Micales & Lyons, 2001, incorporated by reference in its entirety) with the CRG-L2 plasmid 5–2 (containing nucleotides 82–1243 of SEQ ID NO:1) and AFP plasmid (containing nucleotides 726–1401 of the AFP mRNA) in the plasmid pCR4-TOPO (Invitrogen). Sense and antisense probes were synthesized using T7 or SP6 with a MAXIscript kit (Ambion) to generate $^{35}$S uridine triphosphate (UTP)-labeled riboprobes. Hybridized sections were exposed to emulsion (NTB-2; Eastman Kodak) in the dark for 2 weeks before developing. After they were developed, the sections were counterstained with hematoxylin, mounted and viewed under both light-field and dark-field illumination.

Multiple Tissue cDNA Panel. The mouse and human tissue cDNA panels (Clontech) were screened following manufacturer's instructions. After 28 cycles, 5 µl aliquots were removed at various timepoints. The mouse panel was screened with primers, GSP-970 and GSP-1241 (see RACE section for primer sequences), and the human panel was screened with primers, hCRGL2-C [5'-AGGGCCCACCAGGGCAGAAG-3'] (SEQ ID NO:11) and hCRGL2D [5'-ACATGCTTGGCTGCCGAGGG-3'] (SEQ ID NO:12).

Human Tissue. Human tissue and serum was procured from the University of Wisconsin Surgical Pathology department, National Disease Research Interchange, and the NCI Cooperative Human Tissue Network. All samples analyzed were primary tissues. As required by our IRB protocol, the identity of the patients was unknown. The excess tissue was frozen after surgery and stored at −70° C.

Results

Cloning of CRG-L2 using Rapid Amplification of cDNA Ends. By representational difference analysis, a 282 bp fragment of an uncharacterized mRNA was isolated (Graveel et al., 2001). Using RT-PCR analysis with primers located in the RDA fragment, this mRNA showed elevated expression in mouse liver tumors as compared to quiescent, regenerating, or newborn livers (FIG. 1a). The low level of expression in the regenerating livers suggested the possibility that the increased expression was tumor-specific and would not occur in non-tumorigenic proliferative states of human liver, such as cirrhosis or hepatitis. The complete cDNA was obtained via Rapid Amplification of cDNA Ends (RACE). Products from both 5' and 3' RACE were subcloned and sequenced. Sequencing the 3' RACE products revealed three fragments which were identical at their 5' ends due to the fixed location of the gene-specific primer. However, these fragments differed at their 3' ends, with the longer fragments containing, but extending past, the sequence of the shorter fragments. Each fragment contained a polyA tail at its 3' end, indicating that there are multiple polyadenylation sites. The 5' RACE products were all identical. By conceptually combining the 5' and 3' RACE products, three mRNAs were identified that contained alternative 3'UTRs (FIG. 1b). The putative start codon is at nucleotide 25 and the putative stop codon at nucleotide 1344 (see SEQ ID NO:1). Because it was known that this mRNA was upregulated in murine liver tumors yet the function was unknown, this novel mRNA was named Cancer Related Gene-Liver 2 (CRG-L2).

To confirm the presence of all three of the murine CRG-L2 mRNAs and to determine which mRNA is predominantly expressed, a Northern blot hybridization was performed using mRNA from quiescent livers and four individual liver tumors. A 1 kb fragment of the CRG-L2 open reading frame was used as a probe and four mRNAs were observed (FIG. 1c). The 2.4, 3.0, and 5.5 kb mRNAs (designated as A, B, and C respectively in FIG. 1c) correspond to the 1967, 2380, and 4365 bp cloned cDNAs. The size of the observed mRNAs was longer than the RACE cDNA products due to the polyA tails. A fourth mRNA (designated as D) of approximately 10 kb was faintly detected but was not cloned via RACE presumably due to its length. As expected based on previous RT-PCR results, none of the mRNAs were observed in the quiescent livers. The 5.5 kb mRNA was the predominant form in the liver tumors and thus the sequence of the 4365 nt mRNA has been deposited in Genbank as CRG-L2 (AF548022, SEQ ID NO:1).

To determine the structure of the CRG-L2 gene, the sequence of the mRNA was aligned to mouse chromosome 9 (31 cM) using the Jackson Laboratory and Ensembl Mouse Genome browsers (FIG. 1d). The CRG-L2 gene is comprised of 10 exons and nine introns that cover a minimum of 59 kb. An exact measure of the CRG-L2 gene is not yet possible because there are gaps between the contigs that contain the introns between exons 1 and 2 and exons 8 and 9.

Figure 2:
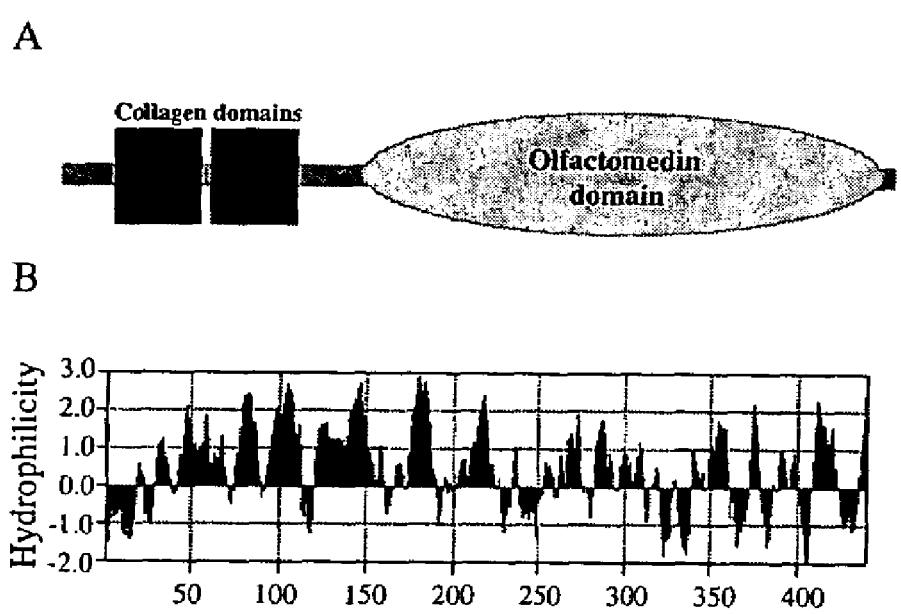
FIG. 2 shows structural features of the CRG-L2 protein. a) CRG-L2 cDNA encodes a protein of 48 kD containing two collagen domains and an olfactomedin domain. b) Hydrophobicity analysis of the putative CRG-L2 protein with the Kyle-Doolittle algorithm. Positive values represent hydrophilic regions and negative values represent hydrophobic regions.

The amino acid sequence (SEQ ID NO:2) of the 47.5 kDa CRG-L2 protein was analyzed by the SMART analysis program (FIG. 2a) and was found to contain two collagen domains near the amino terminus (amino acids 29–88 and 89–149 of SEQ ID NO:2) and a large olfactomedin domain within the C terminus (amino acid 189–433 of SEQ ID NO:2). Hydrophobicity analysis of the CRG-L2 protein revealed hydrophobic sequences within the first thirty amino acids of the amino terminus, which represent a leader sequence, suggesting that CRG-L2 is secreted (FIG. 2b). A serine was also present at amino acid 21 which is anticipated to be the cleavage site of the leader sequence. Regions of high hydrophobicity were also present in the carboxy terminal region, which is anticipated to represent transmembrane domains.

The human sequence for CRG-L2 was pieced together by using the UCSC Human Genome Working Draft (available on the world wide web courtesy of the Center for Biomolecular Science & Engineering at the University of California—Santa Cruz) to align the sequences. The resulting cDNA sequence is presented as SEQ ID NO:3 and the putative amino acid sequence is presented as SEQ ID NO:4. Using the Wilbur-Lipman DNA alignment method the mouse and human open reading frame (ORF) are found to be 82.4% identical. Using the Blosum62 alignment method the mouse and human predicted protein products are found to be 76% identical. Like the murmne protein, the human protein contains two putative collagen domains and one olfactomedin domain, located at amino acids 27–85, 86–145, and 177–395 of SEQ ID NO:4, respectively.

CRG-L2 is localized within chromosome 15q21.2 of the human genome and a similar intron/exon structure is suggested by comparing the mouse cDNA to the human genome. In the human genome data base at NCBI, clone Hs15_10351 (Genbank Accession No. NT_010194), a contig from human chromosome 15, has areas of significant homology to the mouse cDNA sequences. Because this region of the human genome has not been finished in NCBI, the UCSC Human Genome Working Draft was used to align the sequences in piecing together the human sequence for CRG-L2. First, exons of the human CRG-L2 gene were identified by aligning the mouse CRG-L2 ORF to the human genome using the NBLAST program. Next, the identified exons were spliced together and putative introns were excised to form SEQ ID NO:3. SEQ ID NO:4 shows a predicted polypeptide sequence encoded by SEQ ID NO:3. The skilled artisan will appreciate the possibility for some variation in the polynucleotide and polypeptide sequences arising from uncertainty at putative splice sites.

Figure 3:
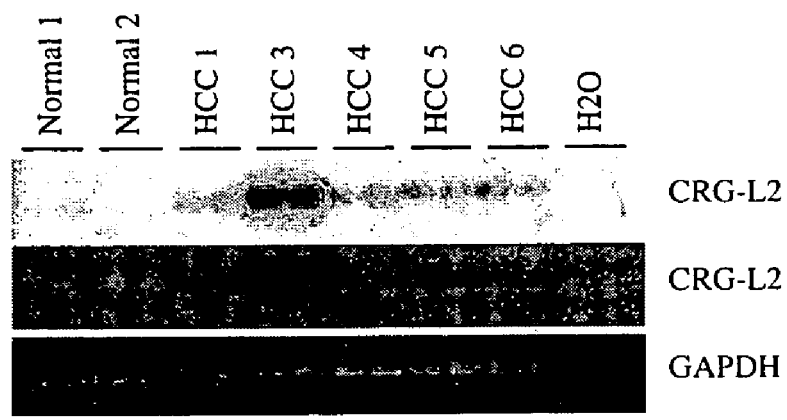
FIG. 3 shows that CRG-L2 expression is increased in human hepatocellular carcinomas. Top panel is a phospho-image of the RT-PCR results measuring CRG-L2 mRNA and middle panel is a longer autoradiographic exposure. Equal loading was confirmed by analysis of GAPDH mRNA. All HCC were classified as moderately differentiated.

CRG-L2 mRNA is upregulated in human hepatocellular carcinomas. As noted above, regions of human chromosome 15 are highly similar to mouse CRG-L2. Based on this similarity, primers were designed to detect human CRG-L2 mRNA. Using these human primers, the level of expression of CRG-L2 was measured in multiple human hepatocellular carcinomas and in normal livers. A combined method of RT-PCR and Southern blot hybridization was used to measure the levels of human CRG-L2. CRG-L2 mRNA was amplified by RT-PCR for 25 cycles and the PCR products were transferred to a nylon membrane that was probed with a fragment of the murine CRG-L2 open reading frame (nucleotides 188–1243 of SEQ ID NO:1). As shown in FIG. 3, CRG-L2 mRNA is essentially undetectable in the normal liver samples but can be detected in all five hepatocellular carcinoma samples (middle panel). Extremely high expression is seen in HCC-2, as seen by the shorter exposure of the film (top panel). Accurate quantitation of the starting mRNA samples was verified by analysis of GAPDH mRNA.

CRG-L2 is upregulated early in liver tumorigenesis. A very important characteristic of a clinical marker for HCC would be early expression during liver tumor development. Because it is difficult to obtain samples corresponding to early states of liver tumors from human cancer patients, we investigated the timing of expression of CRG-L2 using the DEN-treated mouse model. After a single administration of DEN to 12 day old mice, basophilic foci are visible by histological staining at 12 weeks of age. Sequential development of hyperplastic nodules, hepatocellular adenomas, and hepatocellular carcinomas is observed between 12 weeks and 32 weeks of age in male mice (Moore et al., 1981; Vesselinovitch et al., 1985). Therefore, we sacrificed the DEN-treated mice at 20 and 32 weeks of age. At 20 weeks of age, numerous preneoplastic lesions were visible throughout the liver and by 32 weeks the foci had progressed into hepatocellular adenomas/carcinomas (Hanigan et al., 1988). Paraformaldehyde fixed sections from 20 and 32 week livers were probed with either an antisense (to detect CRG-L2 mRNA) or sense (negative control) CRG-L2 probe.

We began by analysis of the 32 week tumors because our RT-PCR results clearly showed that CRG-L2 is upregulated at this stage. Although we expected to detect CRG-L2 mRNA in the 32 week tumors, in situ hybridization can provide additional information that cannot be obtained by RT-PCR analysis. For example, tumor-specific genes may demonstrate a constant level of expression throughout a tumor or the expression can be localized to specific cell types or spatial locations (e.g. the periphery of the tumor). Using in situ hybridization, we observed that CRG-L2 mRNA was upregulated in hepatocytes throughout the entire tumor. We note that CRG-L2 was detected in only 69% (311/453) of the tumors examined using in situ hybridization but was detected in all seven tumors examined by RT-PCR (FIG. 1a). This could be due to the fact that only seven tumors were analyzed in FIG. 1a or because RT-PCR is more sensitive than in situ hybridization.

To determine if CRG-L2 is upregulated at early stages of hepatocarcinogenesis, the expression of CRG-L2 was examined in the preneoplastic foci using in situ hybridization. Interestingly, we found that CRG-L2 mRNA can be detected in preneoplastic foci. The pattern of CRG-L2 expression appears to be consistent throughout the focus with no localization within any individual region. We found that CRG-L2 is highly upregulated in 55% of the foci (220/403) but that there is no obvious histological differences in those foci which do or do not express CRG-L2; e.g. CRG-L2 is upregulated in both basophilic and eosinophilic foci and in foci with extensive fat or collagen deposits. AFP was found to be upregulated in 30% of preneoplastic foci (92/304) although the expression pattern was often restricted to various regions of the focus and not as uniformly distributed as CRG-L2. In other studies, AFP has been shown to be expressed in only 23% of 28 week old DEN-treated B6C3F1 mice (Koen et al., 1983) and 24% of human hepatocellular carcinomas by immunohistochemistry (Borscheri et al., 2001). In comparison to AFP in these studies, CRG-L2 may be a more sensitive marker for the detection of early HCC.

Figure 4:
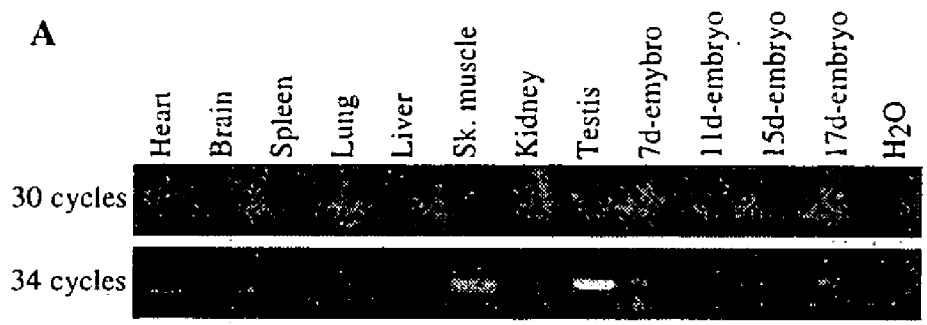
FIG. 4 shows that CRG-L2 expression is restricted in normal tissues. CRG-L2 mRNA was amplified in multiple mouse (a) and human (b) tissues using Multiple Tissue cDNA Panels. Aliquots of the PCR products were taken out at the indicated cycles.
Figure 4:
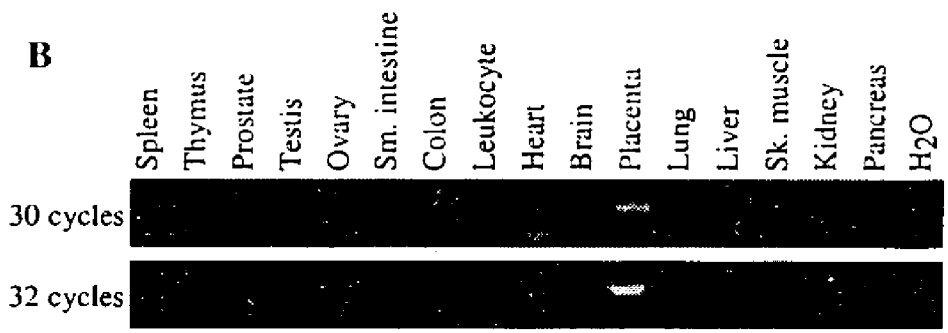

CRG-L2 displays restricted expression in normal tissues. A characteristic of a good clinical marker for HCC is tumor-specific expression; i.e. low expression in all normal tissues not just in the tissue from which the tumor is derived. Although CRG-L2 mRNA was not detected in normal mouse liver, it was possible that the mRNA was expressed in other normal tissues. The expression of CRG-L2 was examined in mouse and human tissues using a multiple tissue cDNA panel. Because performing high numbers of PCR cycles can sometimes obscure differential expression, aliquots of the PCR products were taken out after various cycles (30–34). We found that CRG-L2 is primarily expressed in the mouse testis with moderate expression in skeletal muscle (FIG. 4a). In human tissues, CRG-L2 was expressed primarily in the placenta (FIG. 4b). The pattern of CRG-L2 expression, high in tumors, but normally expressed in testis and placenta, resembles expression patterns of genes known as cancer-testis antigens (CT antigen). Cancer-testis antigens are a group of genes classified by their exclusive expression in the testis and other reproductive tissues and diverse human cancers. The above findings suggest that CRG-L2 is a potential CT antigen.

CRG-L2 is a CT antigen. The examination of CRG-L2 expression revealed that CRG-L2 mRNA is expressed at very low levels in all normal tissues except in the mouse testis and human placenta. Therefore, CRG-L2 falls into a class of genes designated as cancer-testis antigens (CT antigen). The characteristics of CT antigens are a lack of expression in normal tissues, except reproductive tissues, and high levels of expression in a wide range of tumor types. Currently there are more than ten genes identified that are CT antigens, one of which, PAGE, also shows high expression levels in the placenta (Brinkman et al., 1998). Most CT antigens map to the X chromosome, but SCP-1 (Türeci et al., 1998), CT9 (Scanlan et al., 2000), and OY-TES-1 (Ono et al., 2001) map to other chromosomes, as does CRG-L2. CT antigens are intriguing therapeutic targets for immunotherapy because of their limited expression in normal tissues and the fact that the testis and placenta are immune-privileged sites. However, the biological function and the relationship to malignancy of most of these genes is unknown (Ono et al., 2001; Scanlan et al., 2002). With regard to CRG-L2, the protein structure indicates that CRG-L2 belongs to a family of olfactomedin-related proteins, which includes olfactomedin, myocilin/TIGR, noelin-1, and hGC-1. Olfactomedin-related genes have characteristic tissue-restricted expression patterns suggesting a specialized function for each protein (Richards et al., 1998; Zhang et al., 2002). Based on tissue localization of several olfactomedin family members and the function of TIGR/myocilin, it is possible that olfactomedin-related proteins play an important role in protein-protein interactions within the extracellular matrix (Kulkarni et al., 2000). CRG-L2 also contains two collagen domains; proteins that contain collagen domains are also often involved in the structure of the extracellular matrix.

Our results clearly indicate that expression of CRG-L2 is increased in tumors. This increased expression in tumors and restricted pattern of expression in normal tissues indicates that CRG-L2 is a tumor-specific antigen. It is thus anticipated that a patient will display an immunogenic response to CRG-L2, making CRG-L2 a marker that can be detected using blood samples to allow more cost-effective screening of a larger number of high risk patients.

The polynucleotide and polypeptide sequences disclosed herein provide a skilled artisan with the ability to assess using conventional methods the expression levels of the human CRG-L2 gene in an array of tissues and more specifically to monitor the expression of the gene in human liver regions suspected of liver cancer or preneoplastic development as compared to normal human liver tissue. Likewise, antibodies directed to a portion of the human protein can be produced and used as diagnostic agents for assessing protein levels in various human tissues including liver tumors. In addition, over-expressed CRG-L2 from liver tumor cells and preneoplastic liver cells is expected to be secreted into the blood and the blood level of this protein can be easily monitored by various methods known to one of ordinary skill in the art. A patient having liver cancer and preneoplastic development in the liver may also develop an immune response to CRG-L2 and thus an antibody to CRG-L2 may be detected in the blood of the patient.

The present invention is not intended to be limited to the foregoing example, but rather to encompass all such variations and modifications as come within the scope of the appended claims.

REFERENCES (All references listed below are herein incorporated by reference in their entirety)

Borscheri, N., Roessner, A. & Roecken, C. (2001). *Am J Surg Pathol*, 25, 1297–1303.

Brinkman, U., Vasmatzis, G., Lee, B., Yerushalmi, N., Essand, M. & Pastan, I. (1998). *Proc Natl Acac Sci USA*, 95, 10757–10762.

Graveel, C. R., Jatkoe, T., Madore, S. J., Holt, A. L. & Farnham, P. J. (2001). Oncogene, 20, 2704–2712.

Hanigan, M. H., Kemp, C. J., Ginsler, J. J. & Drinkwater, N. R. (1988). *Carcinogenesis*, 9, 885–890.

Koen, H., Pugh, T. D., Nychka, D. & Goldfarb, S. (1983). *Cancer Res*, 43, 702–708.

Kulkarni, N., Karavanich, C. A., Atchley, W. R. & Anholt, R. R. H. (2000). Genet. Res., 76, 41–50.

Lukas, E. R., Bartley, S. M., Graveel, C. R., Diaz, Z. M., Dyson, N., Harlow, E., Yamasaki, L. & Farnham, P. J. (1999). *Mol. Carcino.*, 25, 295–303.

Micales, B. K. & Lyons, G. E. (2001). *Methods*, 23,313–323.

Moore, M. R., Drinkwater, N. R., Miller, E. C., Miller, J. A. & Pitot, H. C. (1981). *Cancer Res*, 41, 1585–1593.

Ono, T., Kurashige, T., Harada, N., Noguchi, Y., Saika, T., Niikawa, N., Aoe, M., Nakamura, S., Higashi, T., Hiraki, A., Wada, H., Kumon, H., Old, L. & Nakayama, E. (2001). *Proc. Natl. Acad. Sci. USA*, 98, 3282–3287.

Richards, J. E., Ritch, R., Lichter, P. R., Rozsa, F. W., Stringham, H. M., Caronia, R. M., Johnson, D., Abundo, G. P., Willcockson, J., Downs, C. A., Thompson, D. a., Musarella, M. A., Gupta, N., Othman, M. I., Torrez, D. M., Herman, S. B., Wong, D. J., Higashi, M. & Boehnke, M. (1998). *Opthalmology*, 105, 1698–1707.

Rigby, P. W. J., Dieckmann, M., Rhoades, C. & Berg, P. (1977). *J. Mol. Biol.*, 113,237–251.

Scanlan, M. J., Altorki, N. K., Gure, A. O., Williamson, B., Jungbluth, A., Chen, Y. T. & Old, L. J. (2000). *Cancer Lett*, 150, 155–164.

Scanlan, M. J., Gordon, C. M., Williamson, B., Lee, S. -Y., Chen, Y. -T., Stockert, E., Jungbluth, A., Ritter, G., Jäger, D., Jäger, E., Knuth, A. & Old, L. J. (2002). *Int. J. Cancer*, 98, 485–492.

Türeci, O., Sahin, U., Zwick, C., Koslowski, M., Seitz, G. & Pfreundschuh, M. (1998). *Proc Natl Acad Sci USA*, 95, 5211–5216.

Vesselinovitch, S. D., Hacker, H. J. & Bannasch, P. (1985). *Cancer Res*, 45, 2774–2780.

Zhang, J., Liu, W. -L., Tang, D. C., Chen, L., Wang, M., Pack, S. D., Zhuang, Z. & Rodgers, G. P. (2002). *Gene*, 283, 83–93.

We claim:

1. An isolated polypeptide comprising amino acids 22–400 of SEQ ID NO:4.

2. The isolated polypeptide of claim 1, wherein the polypeptide consists amino acids 22–400 of SEQ ID NO:4.

3. An isolated polypeptide comprising the amino acid sequence of SEQ ID NO:4.

4. The isolated polypeptide of claim 3, wherein the polypeptide consists of the amino acid sequence of SEQ ID NO:4.

* * * * *

UNITED STATES PATENT AND TRADEMARK OFFICE
CERTIFICATE OF CORRECTION

PATENT NO. : 7,129,328 B2 Page 1 of 1
APPLICATION NO. : 10/620532
DATED : October 31, 2006
INVENTOR(S) : Peggy J. Farnham et al.

It is certified that error appears in the above-identified patent and that said Letters Patent is hereby corrected as shown below:

Column 11, Line 17 "murmne" should be -- murine --

Signed and Sealed this

Third Day of April, 2007

JON W. DUDAS
*Director of the United States Patent and Trademark Office*

SEQUENCE LISTING

<160> NUMBER OF SEQ ID NOS: 12

<210> SEQ ID NO 1
<211> LENGTH: 4365
<212> TYPE: DNA
<213> ORGANISM: mouse
<220> FEATURE:
<221> NAME/KEY: CDS
<222> LOCATION: (25)..(1341)
<220> FEATURE:
<221> NAME/KEY: variation
<222> LOCATION: (1937)
<223> OTHER INFORMATION: From this position forward, first variant 3'
      UTR sequence reads aacccattaaaaaaaaaaaaaaaaaaaaagt
<220> FEATURE:
<221> NAME/KEY: variation
<222> LOCATION: (2342)
<223> OTHER INFORMATION: From this position forward, second variant 3'
      UTR sequence reads ccataaaaaaaaaaaaaaaaaaaaaaaaaaaaaaagt

<400> SEQUENCE: 1

```
cacatccgtg cggagagcca ggac atg atg atg atg atg acc tac tcc atg         51
                           Met Met Met Met Met Thr Tyr Ser Met
                            1               5 gtg ccg att cga gtg atg ata gac ctg tgc aac agt acc cag ggc atc         99
Val Pro Ile Arg Val Met Ile Asp Leu Cys Asn Ser Thr Gln Gly Ile
 10              15                  20                  25 tgc ctc aca gga cca ccg ggc cca cca gga cct cca gga gcc ggc ggg        147
Cys Leu Thr Gly Pro Pro Gly Pro Pro Gly Pro Pro Gly Ala Gly Gly
                 30                  35                  40 tta cca ggc cac aat gga tca gat gga cag cct ggt ctc cag ggc cca        195
Leu Pro Gly His Asn Gly Ser Asp Gly Gln Pro Gly Leu Gln Gly Pro
             45                  50                  55 aaa gga gaa aaa gga gca att ggc aag aga gga aaa atg ggg tta cct        243
Lys Gly Glu Lys Gly Ala Ile Gly Lys Arg Gly Lys Met Gly Leu Pro
         60                  65                  70 gga gcc acc gga aat cca ggg gaa aag gga gaa aag gga gat gct ggt        291
Gly Ala Thr Gly Asn Pro Gly Glu Lys Gly Glu Lys Gly Asp Ala Gly
     75                  80                  85 gaa ctg ggt cta cct gga aat gag ggc cca cca ggg cag aaa ggt gac        339
Glu Leu Gly Leu Pro Gly Asn Glu Gly Pro Pro Gly Gln Lys Gly Asp
 90                  95                 100                 105 aag gga gac aaa gga gac gtg tcc aat gac gtg ctt ttg aca ggt gcc        387
Lys Gly Asp Lys Gly Asp Val Ser Asn Asp Val Leu Leu Thr Gly Ala
                110                 115                 120 aaa ggt gac caa ggt ccc cct ggc ccc cct gga cct cca ggg cct cca        435
Lys Gly Asp Gln Gly Pro Pro Gly Pro Pro Gly Pro Pro Gly Pro Pro
            125                 130                 135 ggc cct cct gga agc aga aga tcc aaa ggc cct cgg cca cca aac gtg        483
Gly Pro Pro Gly Ser Arg Arg Ser Lys Gly Pro Arg Pro Pro Asn Val
            140                 145                 150 ttc aac agc cag tgt cca ggg gag acg tgt gtc ata ccc aat gat gat        531
Phe Asn Ser Gln Cys Pro Gly Glu Thr Cys Val Ile Pro Asn Asp Asp
        155                 160                 165 acc ttg gtg gga aga gct gat gag aaa gca aat gaa cgc cat tca cca        579
Thr Leu Val Gly Arg Ala Asp Glu Lys Ala Asn Glu Arg His Ser Pro
170                 175                 180                 185 caa aca gaa tct atg atc act tcc att ggc aac cca gcc caa gtc cta        627
Gln Thr Glu Ser Met Ile Thr Ser Ile Gly Asn Pro Ala Gln Val Leu
                190                 195                 200 aaa gtg aga gag act ttt ggg act tgg atg aga gag tct gct aac aaa        675
Lys Val Arg Glu Thr Phe Gly Thr Trp Met Arg Glu Ser Ala Asn Lys
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     |     | 205 |     |     |     |     | 210 |     |     |     |     | 215 |      |
| agt | gac | gac | cgc | att | tgg | gtg | act | gaa | cat | ttt | tca | ggc | atc | atg | gtg | 723  |
| Ser | Asp | Asp | Arg | Ile | Trp | Val | Thr | Glu | His | Phe | Ser | Gly | Ile | Met | Val |      |
|     |     | 220 |     |     |     |     | 225 |     |     |     |     | 230 |     |     |     |      |
| aag | gag | ttc | aaa | gac | ctg | ccg | gcg | ctc | ctc | aat | agc | agc | ttc | acc | ctc | 771  |
| Lys | Glu | Phe | Lys | Asp | Leu | Pro | Ala | Leu | Leu | Asn | Ser | Ser | Phe | Thr | Leu |      |
|     | 235 |     |     |     |     | 240 |     |     |     |     | 245 |     |     |     |     |      |
| ctc | cac | ctc | cca | cat | tat | ttc | cac | ggc | tgt | ggg | cac | gct | gtt | tac | aac | 819  |
| Leu | His | Leu | Pro | His | Tyr | Phe | His | Gly | Cys | Gly | His | Ala | Val | Tyr | Asn |      |
| 250 |     |     |     |     | 255 |     |     |     |     | 260 |     |     |     |     | 265 |      |
| aac | tct | ctc | tac | tac | cac | aaa | gga | ggc | tcc | aac | acc | ata | gtg | aga | ttt | 867  |
| Asn | Ser | Leu | Tyr | Tyr | His | Lys | Gly | Gly | Ser | Asn | Thr | Ile | Val | Arg | Phe |      |
|     |     |     |     | 270 |     |     |     |     | 275 |     |     |     |     | 280 |     |      |
| gaa | ttt | ggg | aaa | gag | aca | cct | cag | act | ctg | aag | ctg | gaa | aat | gct | ttg | 915  |
| Glu | Phe | Gly | Lys | Glu | Thr | Pro | Gln | Thr | Leu | Lys | Leu | Glu | Asn | Ala | Leu |      |
|     |     |     |     | 285 |     |     |     |     | 290 |     |     |     |     | 295 |     |      |
| tat | ttt | gat | cga | aaa | tac | ctc | ttt | gca | aat | tcc | aag | act | tac | ttc | aac | 963  |
| Tyr | Phe | Asp | Arg | Lys | Tyr | Leu | Phe | Ala | Asn | Ser | Lys | Thr | Tyr | Phe | Asn |      |
|     |     | 300 |     |     |     |     | 305 |     |     |     |     | 310 |     |     |     |      |
| ata | gca | gtg | gat | gag | aag | ggc | atc | tgg | att | atc | tac | gct | tca | agt | gtg | 1011 |
| Ile | Ala | Val | Asp | Glu | Lys | Gly | Ile | Trp | Ile | Ile | Tyr | Ala | Ser | Ser | Val |      |
|     | 315 |     |     |     |     | 320 |     |     |     |     | 325 |     |     |     |     |      |
| gat | ggc | tca | agc | atc | ctt | gta | gca | cag | ctg | gat | ggg | agg | aca | ttc | tcc | 1059 |
| Asp | Gly | Ser | Ser | Ile | Leu | Val | Ala | Gln | Leu | Asp | Gly | Arg | Thr | Phe | Ser |      |
| 330 |     |     |     |     | 335 |     |     |     |     | 340 |     |     |     |     | 345 |      |
| gtg | aca | cag | cac | atc | aac | acc | aca | tac | ccc | aaa | tcc | aag | gct | ggc | aat | 1107 |
| Val | Thr | Gln | His | Ile | Asn | Thr | Thr | Tyr | Pro | Lys | Ser | Lys | Ala | Gly | Asn |      |
|     |     |     |     | 350 |     |     |     |     | 355 |     |     |     |     | 360 |     |      |
| gcc | ttc | ata | gcc | cga | ggg | atc | ctc | tat | gtc | aca | gac | acc | aaa | gat | acg | 1155 |
| Ala | Phe | Ile | Ala | Arg | Gly | Ile | Leu | Tyr | Val | Thr | Asp | Thr | Lys | Asp | Thr |      |
|     |     |     | 365 |     |     |     |     | 370 |     |     |     |     | 375 |     |     |      |
| agg | gtc | acg | ttt | gcc | ttt | gat | ttg | tta | gga | gga | aag | caa | atc | aat | gca | 1203 |
| Arg | Val | Thr | Phe | Ala | Phe | Asp | Leu | Leu | Gly | Gly | Lys | Gln | Ile | Asn | Ala |      |
|     |     |     |     | 380 |     |     |     |     | 385 |     |     |     |     | 390 |     |      |
| aac | ttt | gat | ttc | aga | atg | tcc | cag | tct | gtt | ctt | gcc | atg | ctg | tca | tac | 1251 |
| Asn | Phe | Asp | Phe | Arg | Met | Ser | Gln | Ser | Val | Leu | Ala | Met | Leu | Ser | Tyr |      |
|     | 395 |     |     |     |     | 400 |     |     |     |     | 405 |     |     |     |     |      |
| aac | atg | aga | gat | cag | cat | tta | tac | tcg | tgg | gaa | gat | ggc | cat | ctg | atg | 1299 |
| Asn | Met | Arg | Asp | Gln | His | Leu | Tyr | Ser | Trp | Glu | Asp | Gly | His | Leu | Met |      |
| 410 |     |     |     |     | 415 |     |     |     |     | 420 |     |     |     |     | 425 |      |
| ctc | tat | cct | gtg | cag | ttt | ctg | tca | gcg | gca | tca | agt | cag | cgg |     |     | 1341 |
| Leu | Tyr | Pro | Val | Gln | Phe | Leu | Ser | Ala | Ala | Ser | Ser | Gln | Arg |     |     |      |
|     |     |     |     | 430 |     |     |     |     | 435 |     |     |     |     |     |     |      |

| | |
|---|---|
| tagggttccc tcggctgtct gctccctctc tatactccac attgtctagg gtttggtcaa | 1401 |
| gcccaacaga aagctagccg gtaaaggata cccaggcact cggagcgtaa gcccatgcca | 1461 |
| cgggctcttg cacaagcggc gagtccgctc taagccaggt tgttgaaata gctacagatt | 1521 |
| agaaatggat gtggaagaga tctggtgacc cagtatccct cctcaaactc agcaagttag | 1581 |
| ctctcccccg accgtagcgt ccccatagqt aatacgaaac atctgagtat gactgacatt | 1641 |
| tcctcttcct agatgaaatt ctgtgattct tgcctgatta tatattagaa tgctttctgg | 1701 |
| attctttttt ttttttttct ccacatgtaa gtgagcttac ttgcagcttg aggggtgggc | 1761 |
| ctttcagtga tgacttattt ggtatttagg gaaggtgcac tggctcttat ggcttctaag | 1821 |
| gttttatttt attcataatt tgttattttc tctgaatatt cacctaccac tacagaatga | 1881 |
| tcattgtttt cagctcctaa acacaaatcc aagattaata aacaaacaaa caaaccatga | 1941 |
| atagatacag gctcagaact ctaaatggag ctgcatcagg cccataggcc atctagatgc | 2001 |

-continued

```
tgcaatttct gatcatattg tttgctgctg ggaaagtaaa caggatatct tcagttcgtg    2061
gtcccttttg ccaaggccat gggattgtta tcagagtgtc aaacactaag tggccaataa    2121
tctggttaga agcatggaaa catgatggtt ttttcagaaa acaggcacca tttatactta    2181
ctgtttagaa tgagggaagg caattggctc aaaggccaaa gtcagcttag ctcttttttcc   2241
tgtaccatcg catccctgca cctaagaatc tcgcctcaga gtgtgtcagc agtgaagcag    2301
agccgctctg taaatcctga accattactg cctggccttt acagaaagaa agaaaaaaaa    2361
atgttgacct ttcatctaag gacagggaac gagccaggtt ctcagaaggg ctcactccct    2421
gagtctggtt aggctttcta cggactgaca ggcagcattt tatgtggctt gggctttggc    2481
agagggaaca gctaaggaca gcatcagatg gagtaagaga acctccagcc gtggagatgt    2541
tcactcccac gtggtcctca aagttgggtc tgtcctcttg gatagcaagg atctagttta    2601
attggttcct acaagacctt aaataaccac gttctctgtc aactcattga gttccaggca    2661
ggcctgtgga gcttcaaaga ggaagctgtg gatttcatcg cccccccccc ccggaatata    2721
gaaaaagaca ctacagaaac tgtccaggaa agactggcca gctgttccaa acccactctc    2781
agtgggcctg tgacctggtt tagttttttt aatagaagca tcttgaggct tggggtatgc    2841
attttaacta tttaactttc cctgccctct gaaagcaccc aggcagctgt tactggtgaa    2901
cctgttgagt tctcaaggtc atgggtccca aagcttcccc acttcttgat tagatggttt    2961
tgcagttggt catcacagct tttaaagata ttctctcaga ttcatttgtt gcaatgtaga    3021
gttctaatgt tttatcagtg tatctaatga atggtattgt tcttttaaag tatttaaata    3081
tgagatactg tttctgagtg cggtagacct ggatatacat ataattccat tttttttatta   3141
tttagtagca ttgctgagaa tagatacaat actaattgta catacaagca aaatagttta    3201
gttattgaat tagctcattt ttaatatctg aactagcaaa tgtcttagct ttcctttact    3261
tttttctttc ttttccttttc ttttctcttc ttttcctttc tttcctttcc ttttcttttc   3321
tttttttttaa agcaatgtct ttgtgttcgc ccagacttat cacaaactcc tgcttcagat   3381
tcctggggct gggaccacag gcacagtggc tctttgactc tcttaattgt gtgtaaggaa    3441
tcatacatat actcacgatt agagaaactc gtctgaagat tttgtttctt ttcatggttg    3501
tttcttttctt tctttctttc tttctttctt tcgttatagt gtagtgggat tagaacaagt   3561
aaggttgact ggtgtttaat gaatttatct ttgcagaagg aaaggaatta aggttttatt    3621
ccttttcttg caaacaggac ttcattctat atcactcaac acagtgtttc aggctcactg    3681
ctaaaatagt gtgcacatct tatattttta aatgaagata gtaatcaacc ctgctgtcac    3741
ttgtagccaa gctgttctaa aagcacttca tttatgtctg tatgaaatca agtgattctc    3801
caattcctct gaaatctaaa gtagatacca ttatactaga aaccacacct tccagcttca    3861
aaggtaggcc agactcaaca tttacaaagc atttctatta actaatatag agtccaacta    3921
aggttgcaga gttggctctg gcctcaatgt atcatgtatc aatgtatcag agaacgtggt    3981
ccgggctgaa tatttcagat caattctggt gctgggctca ttcgaagtct ttttacccctc   4041
ataatcaaat gacaaggtga gatgacaaat gaggaagcac agtccttgaa aagtcactcg    4101
tcatcctcca agcatagcaa gtaccttact caggcattgc ctgtctggtg ttgagctacc    4161
tgaaggaaaa gtgggggggtg gagctcttca gttttcatca gtgctgtggc cttatttatc   4221
tcataatctc ccatcagtaa ccacagattc taaacgacca gcaagtaaca gttgtaagta    4281
gtaaaataaa attatcctga atataatcac aaaaaaaaaa aaaaaaaaaa aagaaaaaaa    4341
```
aaaaaaaaaa aaaaaaaaaa aagt                                                4365

<210> SEQ ID NO 2
<211> LENGTH: 439
<212> TYPE: PRT
<213> ORGANISM: mouse

<400> SEQUENCE: 2

Met Met Met Met Met Thr Tyr Ser Met Val Pro Ile Arg Val Met Ile
1               5                   10                  15

Asp Leu Cys Asn Ser Thr Gln Gly Ile Cys Leu Thr Gly Pro Pro Gly
            20                  25                  30

Pro Pro Gly Pro Pro Gly Ala Gly Gly Leu Pro Gly His Asn Gly Ser
        35                  40                  45

Asp Gly Gln Pro Gly Leu Gln Gly Pro Lys Gly Glu Lys Gly Ala Ile
50                  55                  60

Gly Lys Arg Gly Lys Met Gly Leu Pro Gly Ala Thr Gly Asn Pro Gly
65                  70                  75                  80

Glu Lys Gly Glu Lys Gly Asp Ala Gly Glu Leu Gly Leu Pro Gly Asn
                85                  90                  95

Glu Gly Pro Pro Gly Gln Lys Gly Asp Lys Gly Asp Lys Gly Asp Val
            100                 105                 110

Ser Asn Asp Val Leu Leu Thr Gly Ala Lys Gly Asp Gln Gly Pro Pro
        115                 120                 125

Gly Pro Pro Gly Pro Pro Gly Pro Pro Gly Pro Pro Gly Ser Arg Arg
130                 135                 140

Ser Lys Gly Pro Arg Pro Pro Asn Val Phe Asn Ser Gln Cys Pro Gly
145                 150                 155                 160

Glu Thr Cys Val Ile Pro Asn Asp Asp Thr Leu Val Gly Arg Ala Asp
                165                 170                 175

Glu Lys Ala Asn Glu Arg His Ser Pro Gln Thr Glu Ser Met Ile Thr
            180                 185                 190

Ser Ile Gly Asn Pro Ala Gln Val Leu Lys Val Arg Glu Thr Phe Gly
        195                 200                 205

Thr Trp Met Arg Glu Ser Ala Asn Lys Ser Asp Asp Arg Ile Trp Val
210                 215                 220

Thr Glu His Phe Ser Gly Ile Met Val Lys Glu Phe Lys Asp Leu Pro
225                 230                 235                 240

Ala Leu Leu Asn Ser Ser Phe Thr Leu Leu His Leu Pro His Tyr Phe
                245                 250                 255

His Gly Cys Gly His Ala Val Tyr Asn Asn Ser Leu Tyr Tyr His Lys
            260                 265                 270

Gly Gly Ser Asn Thr Ile Val Arg Phe Glu Phe Gly Lys Glu Thr Pro
        275                 280                 285

Gln Thr Leu Lys Leu Glu Asn Ala Leu Tyr Phe Asp Arg Lys Tyr Leu
290                 295                 300

Phe Ala Asn Ser Lys Thr Tyr Phe Asn Ile Ala Val Asp Glu Lys Gly
305                 310                 315                 320

Ile Trp Ile Ile Tyr Ala Ser Ser Val Asp Gly Ser Ser Ile Leu Val
                325                 330                 335

Ala Gln Leu Asp Gly Arg Thr Phe Ser Val Thr Gln His Ile Asn Thr
            340                 345                 350

Thr Tyr Pro Lys Ser Lys Ala Gly Asn Ala Phe Ile Ala Arg Gly Ile
        355                 360                 365

```
Leu Tyr Val Thr Asp Thr Lys Asp Thr Arg Val Thr Phe Ala Phe Asp
    370                 375                 380

Leu Leu Gly Gly Lys Gln Ile Asn Ala Asn Phe Asp Phe Arg Met Ser
385                 390                 395                 400

Gln Ser Val Leu Ala Met Leu Ser Tyr Asn Met Arg Asp Gln His Leu
                405                 410                 415

Tyr Ser Trp Glu Asp Gly His Leu Met Leu Tyr Pro Val Gln Phe Leu
            420                 425                 430

Ser Ala Ala Ser Ser Gln Arg
            435

<210> SEQ ID NO 3
<211> LENGTH: 1203
<212> TYPE: DNA
<213> ORGANISM: human
<220> FEATURE:
<221> NAME/KEY: CDS
<222> LOCATION: (1)..(1200)

<400> SEQUENCE: 3 atg ctg atg atg atg acc tac tcc atg gtg ccg atc cga gtg atg gtg      48
Met Leu Met Met Met Thr Tyr Ser Met Val Pro Ile Arg Val Met Val
1               5                   10                  15 gac ctg tgc aac agc acc aag ggc atc tgc ctc aca gga cct ccg gga      96
Asp Leu Cys Asn Ser Thr Lys Gly Ile Cys Leu Thr Gly Pro Pro Gly
                20                  25                  30 gcc ggc ggg ttg cca gga cac aac gga ttg gat gga cag cct ggt cct     144
Ala Gly Gly Leu Pro Gly His Asn Gly Leu Asp Gly Gln Pro Gly Pro
            35                  40                  45 cag ggc cca aaa gga gaa aaa gga gca aat gga aaa aga gga aaa atg     192
Gln Gly Pro Lys Gly Glu Lys Gly Ala Asn Gly Lys Arg Gly Lys Met
        50                  55                  60 ggg ata cct gga gct gca gga aat cca ggg gaa agg gga gaa aag gga     240
Gly Ile Pro Gly Ala Ala Gly Asn Pro Gly Glu Arg Gly Glu Lys Gly
65                  70                  75                  80 gac cat ggt gaa ctg ggc ctg cag gga aat gag ggc cca cca ggg cag     288
Asp His Gly Glu Leu Gly Leu Gln Gly Asn Glu Gly Pro Pro Gly Gln
                85                  90                  95 aag gga gaa aag ggt gac aaa gga gat gtg tcc aac gac gtg ctc ctg     336
Lys Gly Glu Lys Gly Asp Lys Gly Asp Val Ser Asn Asp Val Leu Leu
            100                 105                 110 ggt gcc aaa ggt gac caa ggc cca ccc ggt cca cct ggg ccc cca ggc     384
Gly Ala Lys Gly Asp Gln Gly Pro Pro Gly Pro Pro Gly Pro Pro Gly
        115                 120                 125 cct cca ggt cct cca ggg ccc cct gga agc aga aga gcc aaa ggc cct     432
Pro Pro Gly Pro Pro Gly Pro Pro Gly Ser Arg Arg Ala Lys Gly Pro
    130                 135                 140 cgg cag cca agc atg ttc aac ggc cag tgc cca ggt gag act tgt gcc     480
Arg Gln Pro Ser Met Phe Asn Gly Gln Cys Pro Gly Glu Thr Cys Ala
145                 150                 155                 160 ata cca aat gat gat acc ttg gtt gga aaa gct gat gag aaa gcc aaa     528
Ile Pro Asn Asp Asp Thr Leu Val Gly Lys Ala Asp Glu Lys Ala Lys
                165                 170                 175 tcc atg atc act tcc att gga aac cca gtg caa gta ctg aaa gtg aca     576
Ser Met Ile Thr Ser Ile Gly Asn Pro Val Gln Val Leu Lys Val Thr
            180                 185                 190 gag aca ttt ggg act tgg ata aga gag tct gct aac aag agt gat gac     624
Glu Thr Phe Gly Thr Trp Ile Arg Glu Ser Ala Asn Lys Ser Asp Asp
        195                 200                 205 cgg att tgg gtg aca gag cat ttt tca ggt cca cct tcc ata cta ttt     672
```

```
Arg Ile Trp Val Thr Glu His Phe Ser Gly Pro Pro Ser Ile Leu Phe
    210                 215                 220 cca tgg ctg tgg gca cgt tgt tta caa caa ctc tct cta cta cca caa      720
Pro Trp Leu Trp Ala Arg Cys Leu Gln Gln Leu Ser Leu Leu Pro Gln
225                 230                 235                 240 agg gga ttt gaa ttt ggc cag gaa aca tcc caa act ctg aag ctt gaa      768
Arg Gly Phe Glu Phe Gly Gln Glu Thr Ser Gln Thr Leu Lys Leu Glu
                245                 250                 255 aat gcc ttg tat ttt gat cga aaa tac ctt ttt gca aat tcc aaa act      816
Asn Ala Leu Tyr Phe Asp Arg Lys Tyr Leu Phe Ala Asn Ser Lys Thr
            260                 265                 270 tac ttc aat cta gct gta gat gaa aag ggc ctt tgg att atc tat gcg      864
Tyr Phe Asn Leu Ala Val Asp Glu Lys Gly Leu Trp Ile Ile Tyr Ala
        275                 280                 285 tca agt gtg gac ggc tcg agc att ctt gta gca caa ctg gat gag agg      912
Ser Ser Val Asp Gly Ser Ser Ile Leu Val Ala Gln Leu Asp Glu Arg
    290                 295                 300 aca ttc tca gtg gtg caa cac gtc aat acc acg tac cct aaa tcc aag      960
Thr Phe Ser Val Val Gln His Val Asn Thr Thr Tyr Pro Lys Ser Lys
305                 310                 315                 320 gct ggc aac gcc ttc att gcc cga gga atc ctc tat gtc aca gac acc     1008
Ala Gly Asn Ala Phe Ile Ala Arg Gly Ile Leu Tyr Val Thr Asp Thr
                325                 330                 335 aaa gat atg agg gtc aca ttt gcc ttt gat ttg tta gga ggg aaa cag     1056
Lys Asp Met Arg Val Thr Phe Ala Phe Asp Leu Leu Gly Gly Lys Gln
            340                 345                 350 atc aat gca aac ttt gat tta aga act tcc cag tct gtt ctt gcc atg     1104
Ile Asn Ala Asn Phe Asp Leu Arg Thr Ser Gln Ser Val Leu Ala Met
        355                 360                 365 tta gca tac aac atg aga gat cag cat tta tat tca tgg gaa gat ggc     1152
Leu Ala Tyr Asn Met Arg Asp Gln His Leu Tyr Ser Trp Glu Asp Gly
    370                 375                 380 cat tta atg ctt tat cct gtg cag ttt ttg tca act acc tta aat cag     1200
His Leu Met Leu Tyr Pro Val Gln Phe Leu Ser Thr Thr Leu Asn Gln
385                 390                 395                 400 tga                                                                  1203

<210> SEQ ID NO 4
<211> LENGTH: 400
<212> TYPE: PRT
<213> ORGANISM: human

<400> SEQUENCE: 4

Met Leu Met Met Met Thr Tyr Ser Met Val Pro Ile Arg Val Met Val
1               5                   10                  15

Asp Leu Cys Asn Ser Thr Lys Gly Ile Cys Leu Thr Gly Pro Pro Gly
                20                  25                  30

Ala Gly Gly Leu Pro Gly His Asn Gly Leu Asp Gly Gln Pro Gly Pro
            35                  40                  45

Gln Gly Pro Lys Gly Glu Lys Gly Ala Asn Gly Lys Arg Gly Lys Met
        50                  55                  60

Gly Ile Pro Gly Ala Ala Gly Asn Pro Gly Glu Arg Gly Glu Lys Gly
65                  70                  75                  80

Asp His Gly Glu Leu Gly Leu Gln Gly Asn Glu Gly Pro Pro Gly Gln
                85                  90                  95

Lys Gly Glu Lys Gly Asp Lys Gly Asp Val Ser Asn Asp Val Leu Leu
            100                 105                 110

Gly Ala Lys Gly Asp Gln Gly Pro Pro Gly Pro Pro Gly Pro Pro Gly
```

```
                    115                 120                     125
Pro Pro Gly Pro Pro Gly Pro Gly Ser Arg Arg Ala Lys Gly Pro
    130                 135                 140

Arg Gln Pro Ser Met Phe Asn Gly Gln Cys Pro Gly Glu Thr Cys Ala
145                 150                 155                 160

Ile Pro Asn Asp Asp Thr Leu Val Gly Lys Ala Asp Glu Lys Ala Lys
                165                 170                 175

Ser Met Ile Thr Ser Ile Gly Asn Pro Val Gln Val Leu Lys Val Thr
                180                 185                 190

Glu Thr Phe Gly Thr Trp Ile Arg Glu Ser Ala Asn Lys Ser Asp Asp
                195                 200                 205

Arg Ile Trp Val Thr Glu His Phe Ser Gly Pro Pro Ser Ile Leu Phe
    210                 215                 220

Pro Trp Leu Trp Ala Arg Cys Leu Gln Gln Leu Ser Leu Leu Pro Gln
225                 230                 235                 240

Arg Gly Phe Glu Phe Gly Gln Glu Thr Ser Gln Thr Leu Lys Leu Glu
                245                 250                 255

Asn Ala Leu Tyr Phe Asp Arg Lys Tyr Leu Phe Ala Asn Ser Lys Thr
                260                 265                 270

Tyr Phe Asn Leu Ala Val Asp Glu Lys Gly Leu Trp Ile Ile Tyr Ala
    275                 280                 285

Ser Ser Val Asp Gly Ser Ser Ile Leu Val Ala Gln Leu Asp Glu Arg
    290                 295                 300

Thr Phe Ser Val Val Gln His Val Asn Thr Thr Tyr Pro Lys Ser Lys
305                 310                 315                 320

Ala Gly Asn Ala Phe Ile Ala Arg Gly Ile Leu Tyr Val Thr Asp Thr
                325                 330                 335

Lys Asp Met Arg Val Thr Phe Ala Phe Asp Leu Leu Gly Gly Lys Gln
                340                 345                 350

Ile Asn Ala Asn Phe Asp Leu Arg Thr Ser Gln Ser Val Leu Ala Met
                355                 360                 365

Leu Ala Tyr Asn Met Arg Asp Gln His Leu Tyr Ser Trp Glu Asp Gly
    370                 375                 380

His Leu Met Leu Tyr Pro Val Gln Phe Leu Ser Thr Thr Leu Asn Gln
385                 390                 395                 400

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:PCR primer

<400> SEQUENCE: 5
gcatggcaag aacagactgg                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:PCR primer

<400> SEQUENCE: 6
ggatgagaag ggcatctgga                                              20

<210> SEQ ID NO 7
```

```
<211> LENGTH: 19
<212> TYPE: DNA
<213> ORGANISM: Artificial Sequence
<220> FEATURE:
<223> OTHER INFORMATION: Description of Artificial Sequence:PCR primer

<400> SEQUENCE: 7
caacaacctg gcttagagc                                                    19

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence:PCR primer

<400> SEQUENCE: 8
gccatctgat gctctatcc                                                    19

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:PCR primer

<400> SEQUENCE: 9
catggcaaga acagactggg                                                   20

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence:PCR primer

<400> SEQUENCE: 10
gccaggaaac atcccaaact c                                                 21

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:PCR primer

<400> SEQUENCE: 11
agggcccacc agggcagaag                                                   20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:PCR primer

<400> SEQUENCE: 12
acatgcttgg ctgccgaggg                                                   20
```